United States Patent
Hershberger

(10) Patent No.: US 6,488,713 B1
(45) Date of Patent: Dec. 3, 2002

(54) HIP JOINT PROSTHESIS WITH INTEGRAL BEARING EXTRACTION MEMBER

(75) Inventor: Troy W. Hershberger, Winona Lake, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/842,499

(22) Filed: Apr. 25, 2001

(51) Int. Cl.$^7$ .................................................. A61F 2/34
(52) U.S. Cl. ................... 623/22.11; 623/16.11; 623/18.11
(58) Field of Search .............................. 623/22.1, 22.11, 623/16.11, 18.11, 22.38, 22.24, 22.31

(56) References Cited

U.S. PATENT DOCUMENTS

| | | | |
|---|---|---|---|
| 4,878,916 A | 11/1989 | Rhenter et al. ................ | 623/18 |
| 5,019,105 A | 5/1991 | Wiley .......................... | 623/22 |
| 5,061,271 A | 10/1991 | Van Zile ...................... | 623/20 |
| 5,092,897 A | 3/1992 | Forte .......................... | 623/22 |
| 5,413,603 A | 5/1995 | Noiles et al. ................. | 623/18 |
| 5,443,519 A | 8/1995 | Averill et al. ................. | 623/22 |
| 5,609,648 A * | 3/1997 | Oehy et al. | |
| 5,658,346 A * | 8/1997 | Willi | |
| 5,876,456 A * | 3/1999 | Sederholm et al. | |
| 5,938,702 A * | 8/1999 | Lopez et al. | |
| 6,087,553 A | 7/2000 | Cohen et al. .................. | 623/16 |
| 6,120,546 A * | 9/2000 | Dye et al. | |
| 6,132,469 A | 10/2000 | Schroeder ................ | 623/22.24 |
| 6,231,612 B1 * | 5/2001 | Balay et al. | |
| 6,280,476 B1 | 8/2001 | Metzger et al. | |

FOREIGN PATENT DOCUMENTS

WO   WO00023012   4/2000

OTHER PUBLICATIONS

RingLoc Acetabular Series, Biomet, Inc. product literature, ©1998.
Vision Hip System Acetabular Series, Biomet, Inc. product brochure (C)1996.

* cited by examiner

Primary Examiner—Pedro Philogene
(74) Attorney, Agent, or Firm—William F. Bahret

(57) ABSTRACT

A hip joint prosthesis having a retainer for a modular bearing in an acetabular cup and also having a bearing extraction member mounted in the cup for removal of a primary bearing. One embodiment of the bearing extraction member is a plug which is located in a hole provided in the acetabular cup and which is covered by a polyethylene bearing directly molded into the cup. The plug is an internally threaded plug with a convex head and is adapted to be pulled out of its resting position in the cup with the aid of an extraction tool such that the head of the plug exerts a removal force on the molded polyethylene bearing, causing it to disengage from the cup.

17 Claims, 6 Drawing Sheets

HIP JOINT PROSTHESIS WITH INTEGRAL BEARING EXTRACTION MEMBER

BACKGROUND OF THE INVENTION

This invention relates to surgically implantable hip joint prostheses and, more particularly, to a hip joint prosthesis that combines advantages of modular and nonmodular prostheses.

Artificial joints of the human body, including in particular knee and hip joints, have been available for 50 years or more and have been the subject of intense development for at least the last 20 years. The earliest designs provided metal-to-bone or metal-to-metal contact between the articulating surfaces of a joint. Friction and wear were significantly reduced in subsequent designs by the introduction of ultra-high molecular weight polyethylene (UHMWPE) as a load-bearing surface. For example, a typical hip joint prosthesis has an acetabular cup or shell lined with a polyethylene load-bearing surface which is designed to contact a rounded femoral head made of metal.

A number of different methods of securing a polyethylene liner or bearing in an acetabular cup have been developed over the years, as exemplified by the following patents which are incorporated herein by reference in their entireties:

| Patent No. | Inventor | Issue Date |
| --- | --- | --- |
| 4,878,916 | Rhenter et al. | Nov. 7, 1989 |
| 5,019,105 | Wiley | May 28, 1991 |
| 5,092,897 | Forte | Mar. 3, 1992 |
| 5,443,519 | Averill et al. | Aug. 22, 1995 |
| 6,087,553 | Cohen et al. | Jul. 11, 2000 |

There are two general types of prosthetic components: modular and nonmodular. A nonmodular prosthesis has a bearing secured to a base, e.g., an acetabular cup, during fabrication in the factory, typically by direct compression molding. A modular prosthesis has a prefabricated bearing designed to be attached to the base during surgery.

A modular prosthesis has several advantages over non-modular prostheses, one of which is that an assortment of different prostheses, i.e., different base/bearing combinations, can be created in the operating room from a small inventory of separate bases and bearings of various sizes, shapes and other characteristics. With a modular prosthesis, an orthopedic surgeon can implant an appropriate base for the patient and then fit the patient with several trial bearings in the process of selecting an appropriate primary bearing to attach to the implanted base. Modular bearings are often readily removable, and in such cases they have the further advantage of facilitating revision surgery, which may become necessary in cases of traumatic injury or bearing surface wear, by enabling replacement of the bearing without removing the base.

There are also advantages to a nonmodular prosthesis construction, such as design simplicity due to the absence of a need for a retaining mechanism for a removable bearing, and relatively low cost. An even more significant advantage is that a nonmodular component is virtually immune to micromotion at the interface between the bearing and the base.

Micromotion is very difficult to avoid with modular components due to the typical need for clearances between bearing and base to ensure that they fit together during assembly in the operating room. A very secure locking method may avoid the problem, but nonmodular fabrication of the prosthesis, e.g., direct compression molding of a bearing onto a base, avoids the issue. Unfortunately, a nonmodular prosthesis has heretofore made revision surgery more difficult in that the entire prosthetic component must be removed and replaced. In addition to the extra operating time involved and extraction tools required. such as described in U.S. Pat. No. 4,459,985 to McKay, removal and replacement of the base requires sacrificing the existing fixation to the bone and has associated complications, including possible bone loss or fracture and the difficulty of reestablishing solid fixation. Nevertheless, it is conventional wisdom regarding a nonmodular prosthesis that the bearing component cannot be changed without changing the base component.

SUMMARY OF THE INVENTION

The present invention combines advantages of modular and nonmodular designs by providing a hip joint prosthesis with an integral bearing extraction member for extraction of a bearing from an implanted acetabular cup without disturbing the implanted cup. An extraction member according to the principles of the invention may be implanted as part of an acetabular cup assembly having a modular bearing to facilitate removal of the modular bearing, but is especially useful as part of a nonmodular prosthesis whereby the prosthesis is made convertible in vivo from a nonmodular device to a modular device.

According to one aspect of the invention, the prosthesis includes an acetabular cup having a retainer for a modular bearing, a primary bearing directly molded to the cup, and implantable means for removing the molded primary bearing from the acetabular cup substantially in one piece without disturbing the acetabular cup. A retainer as that term is used herein is a part of the base, i.e., the acetabular cup, that is capable, alone or in conjunction with an auxiliary element or elements, of retaining a modular bearing in place on the base. It may be formed on the base as a one-piece or multi-piece retainer.

According to a further aspect of the invention, a bearing extraction member is mounted in an acetabular cup in contact with a primary bearing as a part of the prosthesis designed to be actuated during revision surgery. Upon actuation, the bearing extraction member forces the primary bearing out of the acetabular cup, after which the primary bearing and extraction member are removed and replaced by a modular bearing. In some cases, conversion to a modular device would be a desirable option even during the primary surgery. It is routine for surgeons to check the patient's range of motion before and after cementing or otherwise permanently affixing a prosthesis of a chosen size in the patient's acetabulum. With a nonmodular prosthesis the surgeon has little recourse but to dislodge the complete prosthesis and remove it and any associated cement if the final range-of-motion check is unsatisfactory. The present invention provides a desirable alternative.

A general object of the present invention is to provide an improved surgically implantable joint prosthesis.

Another object of the present invention is to provide advantages of a nonmodular joint prosthesis, including the virtual absence of micromotion, and yet allow a surgeon performing revision surgery to replace a primary bearing without disturbing the base member and thereby jeopardizing fixation.

Another object of the invention is to extend the lifetime of an artificial joint.

These and other objects and advantages of the present invention will be more apparent upon reading the following detailed description of the preferred embodiment in conjunction with the accompanying drawings.

DETAILED DESCRIPTION OF THE PREFERRED EMBODIMENT

Figure 1:
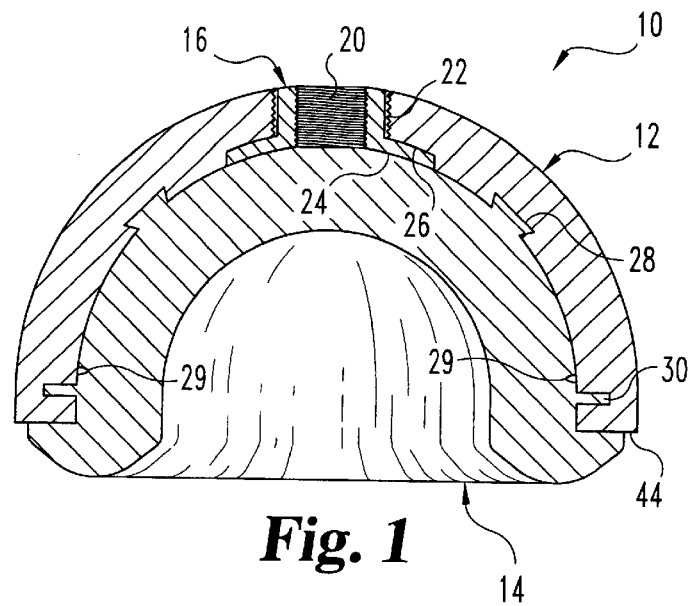
FIG. 1 is a cross-sectional side view of an acetabular cup assembly according to one embodiment of the present invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1A:
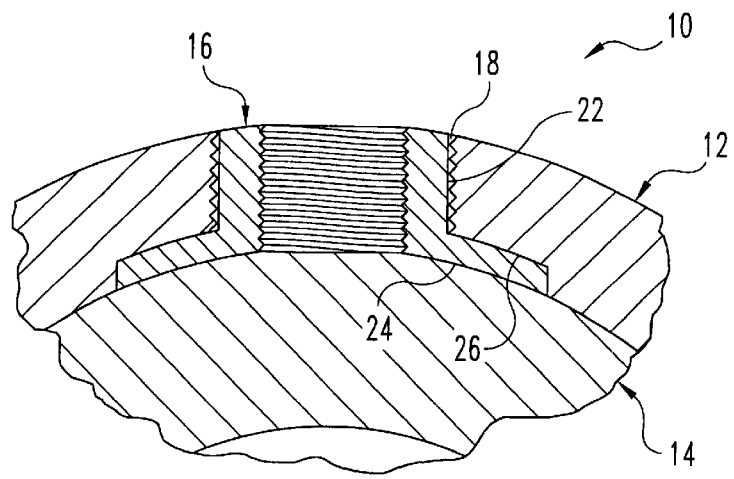
FIG. 1A is a detail drawing of a portion of the acetabular cup assembly of FIG. 1.

Referring to FIGS. 1 and 1A, an acetabular cup assembly 10 includes a shell 12 and a polyethylene bearing 14 which is molded into the shell with a bearing extraction member or bearing removal means 16 in the form of an implantable "puller plug" in place in a threaded apical hole 18 in the shell. The shell is typically made of biocompatible metal such as titanium or cobalt-chromium, and the puller plug may be made of the same material. The plug includes a threaded central opening 20 and an unthreaded cylindrical outer surface 22 and is slidably seated in the hole 18 and axially constrained by a convex annular flange or head 24 which in turn is seated in an annular recess 26 provided for this purpose in the shell. The bearing is preferably formed by direct compression molding of ultra-high molecular weight polyethylene (UHMWPE) into the shell. A peak temperature of approximately 190° C. and a peak pressure of approximately 1000 psi are suitable for formation of the UHMWPE bearing in a direct compression molding press, with a total molding time of 1.5–2 hours out of which the press is at peak pressure and temperature for approximately 20–30 minutes. The pressure and temperature are ramped up to the desired peak levels, held at those levels for the 20–30 minute "soak period," and then ramped down.

The opening 20 in the plug may be filled with polyethylene during the molding process and later cleared of polyethylene as will be described. The shell may be provided with one or more dovetails 28 to receive polyethylene during the molding process and thereby facilitate tight retention of the bearing against the inner surface of the cup after cooling of the polyethylene. Alternatively, or additionally, a number of prongs, barbs or other protrusions 29 may be provided on the inner surface of the shell to facilitate retention of the bearing. For example, 10–20 prongs may be equally spaced circumferentially within shell 12. Such a construction is also useful for securing a preformed bearing insert in the shell. For example, a bearing may be preformed with an outer diameter substantially equal to or slightly greater than the inner diameter of shell 12 and may be shrunk with liquid nitrogen, for example, to fit within the shell without obstruction from the prongs, after which the cooling medium may be removed and the preformed bearing allowed to expand to establish an interference fit with the concave inner surface of the shell. The prongs press into and embed themselves within the bearing insert during such expansion, creating corresponding holes in the bearing in the process, and thereby, along with the concave shell surface contributing to the interference fit, help retain the modular bearing insert in the shell. Alternatively, or additionally, an annular groove 30 may be provided in the shell as a retainer adapted to receive a locking ring and, in conjunction therewith, to retain a modular bearing as a replacement for the primary bearing as will be described. The acetabular cup assembly as just described is designed to be implanted in a patient during a primary hip replacement procedure. A RingLoc® acetabular shell, commercially available from Biomet, Inc., is an example of a shell which has a groove such as described above and which may be modified in accordance with the principles of the present invention.

Figure 2:
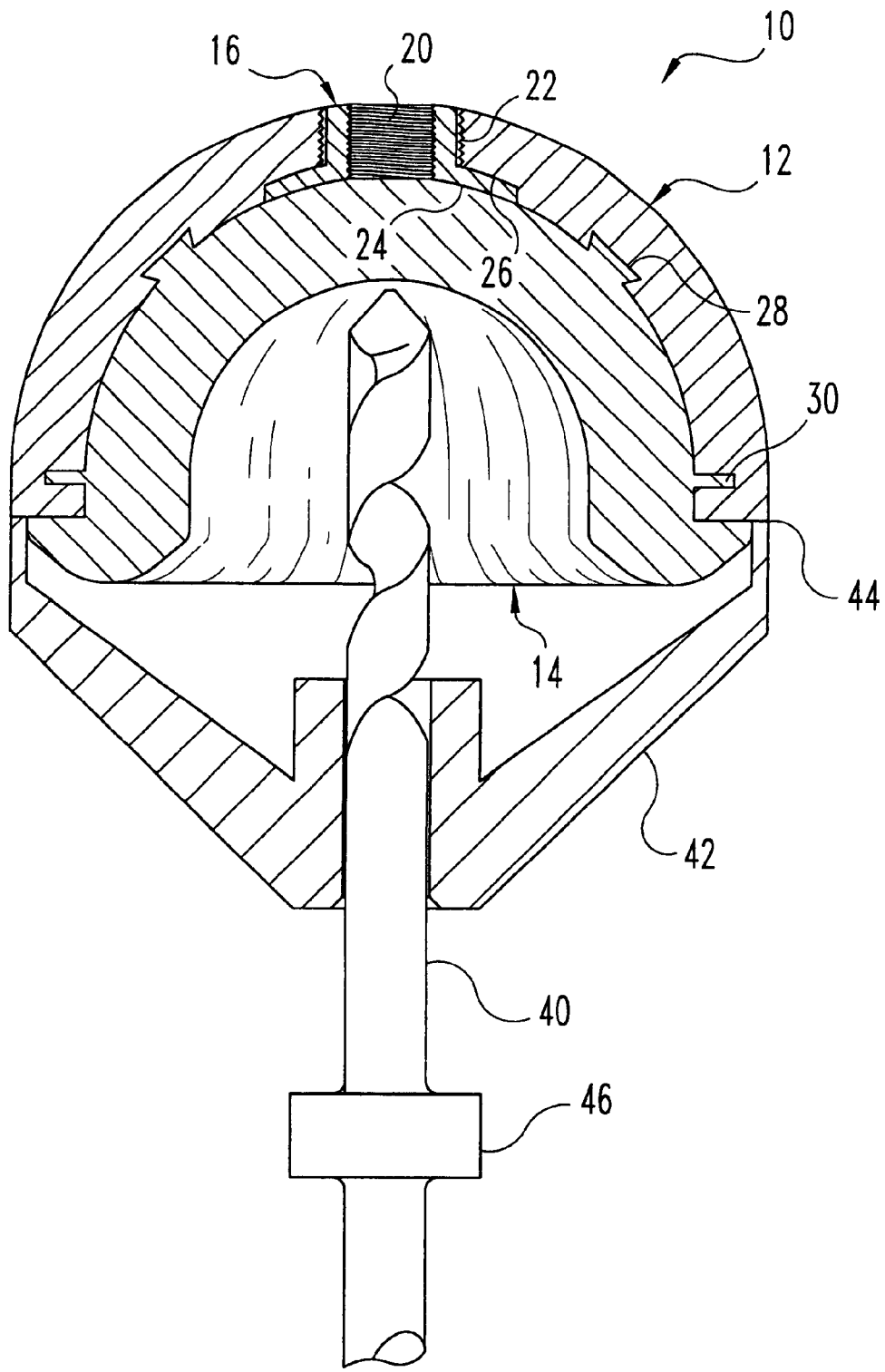
FIG. 2 is a cross-sectional side view of the acetabular cup assembly of FIG. 1 and an associated drill guide in place for performance of a preliminary step in the removal of the primary bearing.

The primary bearing is removable during a revision procedure, as will now be described with reference to FIGS. 2 and 3. A drill bit 40 is slidably received in a drill guide 42 which is adapted to locate on the rim or face 44 of shell 12 as shown in FIG. 2. The drill guide axially aligns the drill bit with the opening in plug 16 and thereby facilitates precision drilling of a hole through the polyethylene bearing and through the polyethylene within plug 16. A drill stop 46 is provided on the drill bit to prevent drilling beyond the plug and into the acetabulum. The drill bit is sized so as to expose the threads in the puller plug after the hole is drilled.

Figure 3:
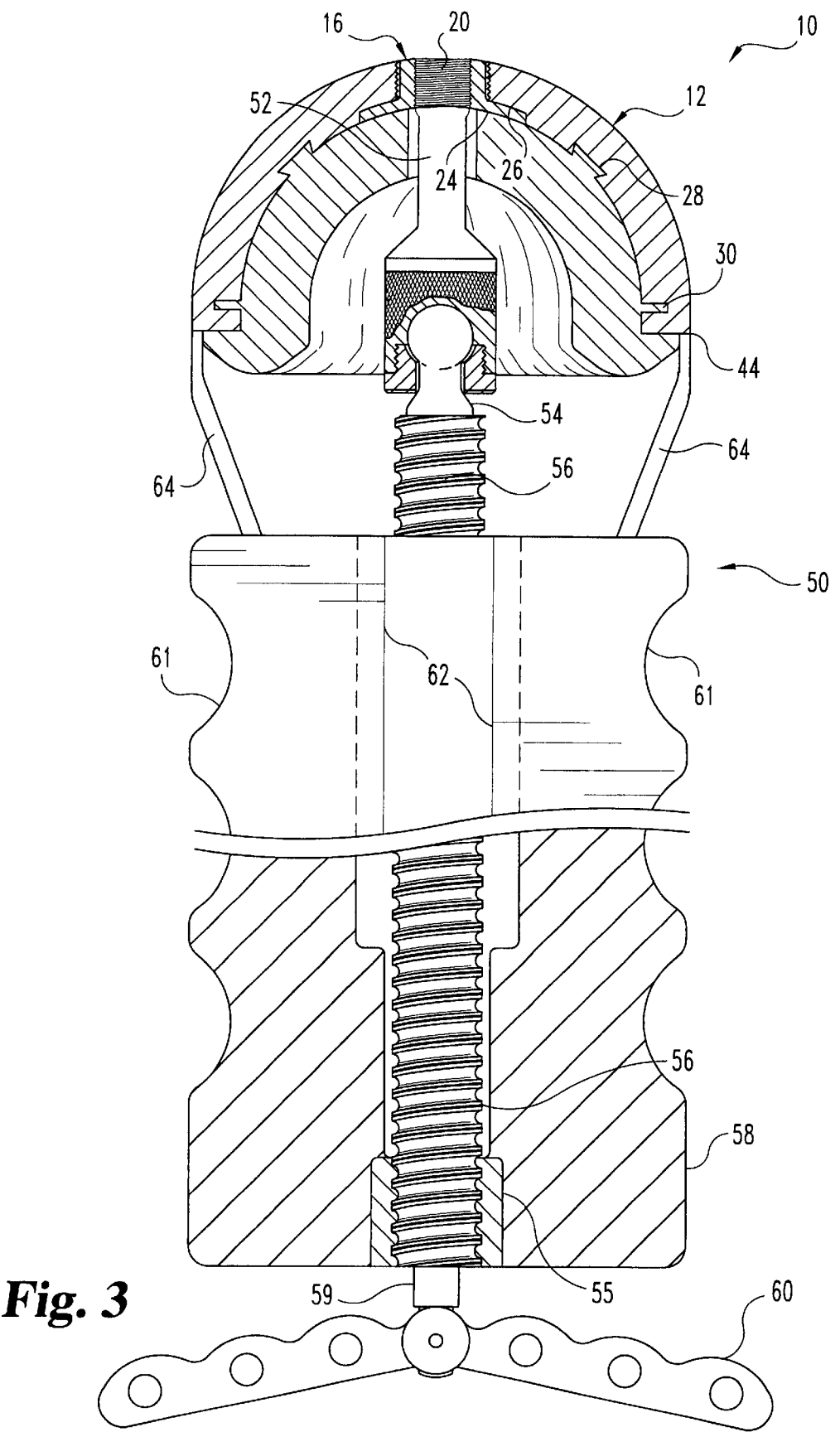
FIG. 3 is a cross-sectional side view of the acetabular cup assembly of FIG. 1 in conjunction with an extractor for removal of the primary bearing.

Referring to FIG. 3, the molded primary bearing can then be removed by pulling plug 16 out of shell 12 with the aid of an extractor 50 adapted to locate on rim 44 of the shell and engage plug 16 as shown in the drawing. The extractor, shown in partial cross-section, is a modified form of a Model RD140080 knee instrument which is commercially available from Biomet, Inc., and includes a threaded nose portion 52 rotatably mounted on the distal end 54 of an Acme screw 56 that is threaded into and supported entirely by a nut 55, which may be made of UHMWPE and is nonrotatably mounted in a metal casing 58. Drive screw 56 is provided on its proximal end 59 with a T-handle 60 for use in turning and thereby axially advancing or retracting the drive screw. T-handle 60 may have a width of approximately 6 inches. The casing is advantageously sized and shaped to serve as a hand grip with individual finger holds 61 as shown in FIG.

3. A suitable length of casing 58 for such purposes is approximately 5 inches, and a suitable width as viewed in FIG. 3 is approximately 2.5 inches. The depth of the casing, i.e., the dimension along a line perpendicular to the plane of the page in FIG. 3, may have a maximum value of approximately half the width of the casing. Further, the casing may have a flattened hexagonal transverse cross-section, with the depth decreasing linearly from lines 62 to the finger holds 61. A pair of axially extending prongs or arms 64 is provided on the distal end of casing 58 as a brace for the extractor.

The nose portion of the extractor and the puller plug are provided with mating threads. Although nose portion 52 and drive screw 56 are both shown as right-hand (RH) threaded, either or both may be left-hand (LH) threaded in other embodiments. It may be useful to have one part RH threaded and the other LH threaded in order to avoid the possibility of friction-related retraction of the nose portion during retraction of the ball screw. The extractor may include a releasable ratchet mechanism (not shown) to prevent clockwise rotation of the ball screw when the ratchet is engaged, thereby allowing a surgeon's grip on the T-handle to be temporarily released for repositioning during retraction of the ball screw.

Figure 4:
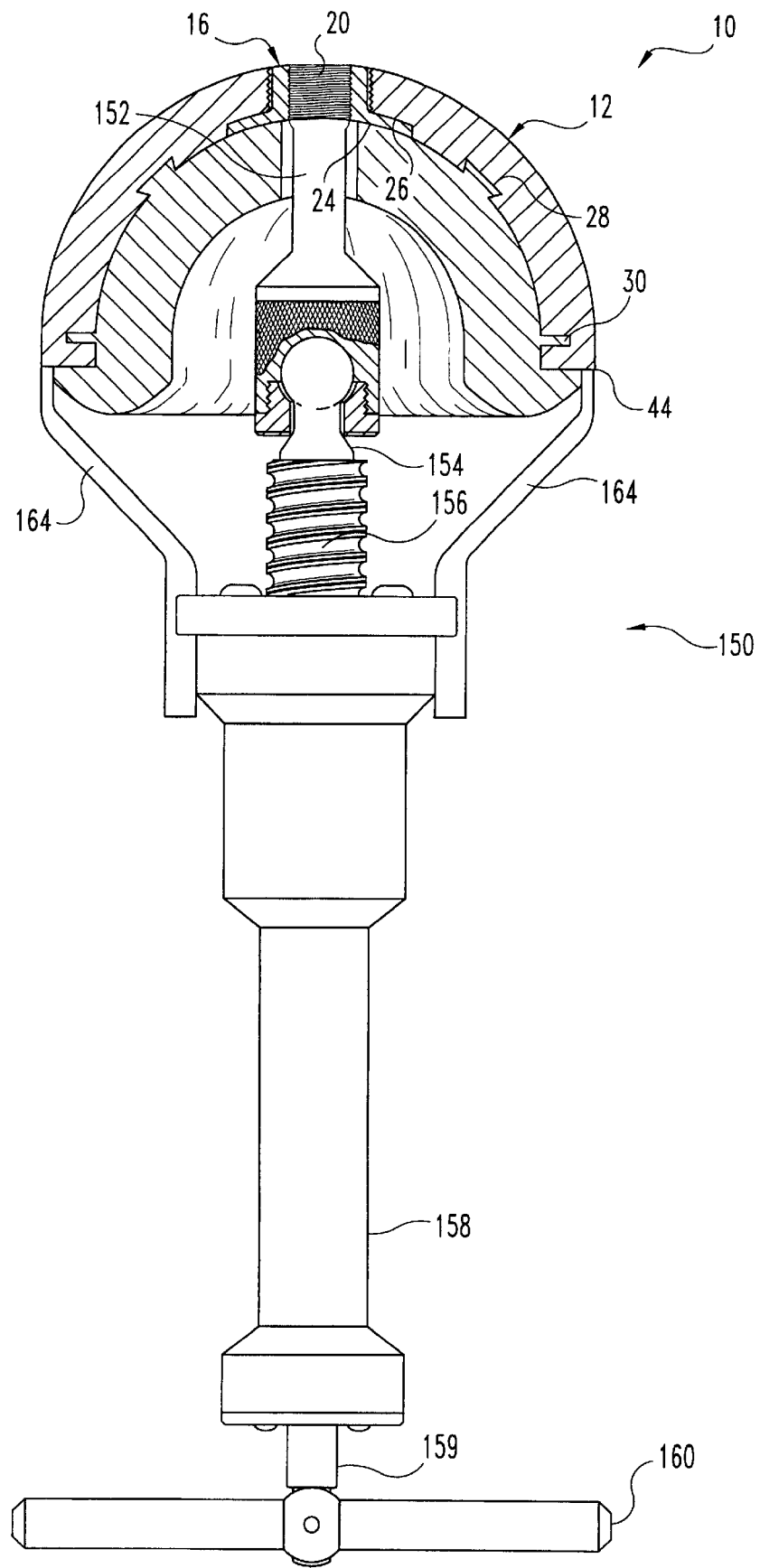
FIG. 4 is a partial cross-sectional side view of an alternative embodiment of an extractor for use with the acetabular cup assembly of FIG. 1.
Figure 5:
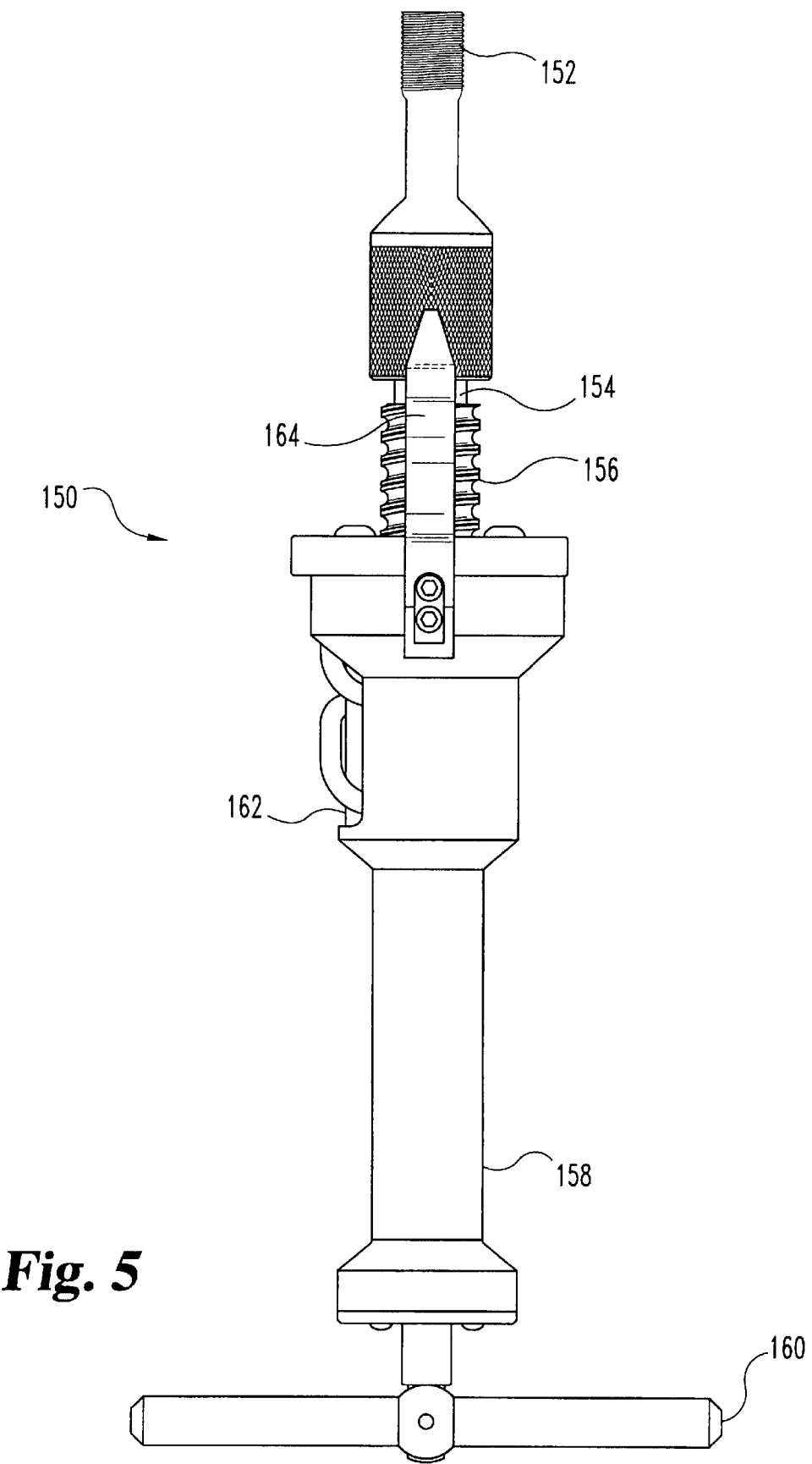
FIG. 5 is a side view of the extractor of FIG. 4.

FIGS. 4 and 5 show an alternative embodiment of an extractor for use with acetabular cup assembly 10 of FIG. 1. Like the extractor of FIG. 3, extractor 150 includes a threaded nose portion 152 rotatably mounted on the distal end 154 of a drive screw 156, in this case a ball screw, that is rotatably mounted in a casing 158 and provided on its proximal end 159 with a T-handle 160. Casing 158 is cylindrical with varying diameter as illustrated. The ball screw is enmeshed with a recirculating ball nut 162 that is nonrotatably mounted in casing 158, which has an axially extending prong or arm 164 on the distal end thereof on either side of the ball screw as a brace for the extractor. A suitable ball screw for such purposes is commercially available from Thomson Saginaw Ball Screw Company, Inc., Saginaw, Mich., as Catalog No. 720426SS. A compatible ball nut is the Thomson Catalog No. 5708278 ball nut. A precision steel ball bushing bearing, Thomson Catalog No. A-81420, is mounted in the proximal end of the casing to rotatably and slidably support the unthreaded proximal end of the ball screw shaft. As with the extractor of FIG. 3, the nose portion of the extractor and the puller plug are provided with mating threads.

Figure 6:
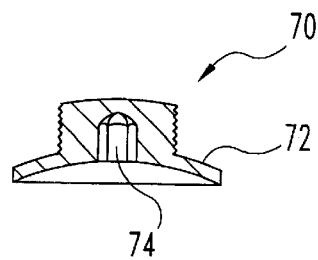
FIG. 6 is a cross-sectional side view of a replacement plug for use with the present invention.

In operation, after the drilling step described above, the drive screw of the extractor is advanced sufficiently to allow the threaded nose portion (52 or 152) to be inserted through the hole in the bearing and screwed into the puller plug by manual rotation of the nose portion, which may have a knurled outer surface, as illustrated in the drawings, to facilitate rotation. The ball screw is then retracted with the aid of the T-handle and thereby exerts a pulling force on the nose portion, which is stationary with respect to plug 16 at this time. Plug 16 is accordingly pulled toward the extractor casing, whereupon the head of the plug exerts a corresponding removal force on the primary bearing, causing it to disengage from the shell. The primary bearing is thus removed substantially in one piece without disturbing the fixation of the shell within the patient's acetabulum. The primary bearing is then replaced with a modular bearing of the type which is designed to be secured with a locking ring inserted into groove 30 in the shell. Prior to insertion of the modular bearing, a locking ring is inserted into the groove, and a threaded plug is inserted into the hole in the shell left vacant by the removal of plug 16. As shown in FIG. 6, a suitable replacement plug 70 for such purposes has an annular flange or head 72 identical to that of plug 16 and has a hexagonal hole 74 for driving the replacement plug into place with an Allen wrench or the like.

Figure 7:
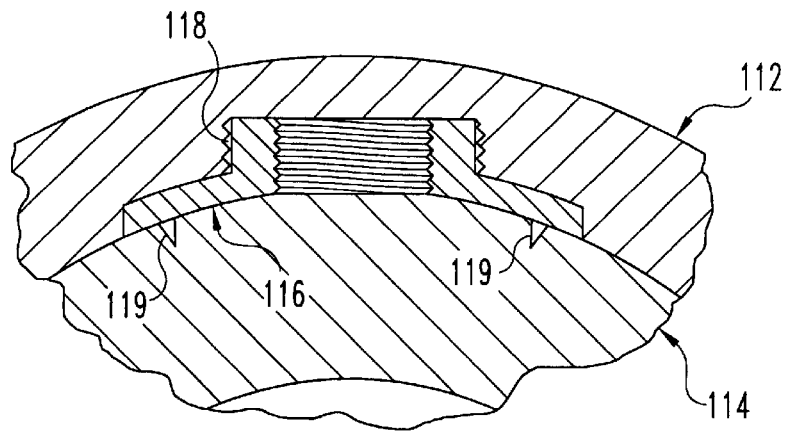
FIG. 7 is a cross-sectional side view of a portion of another embodiment of an acetabular cup assembly according to the present invention.

FIG. 7 illustrates an alternative embodiment of the invention in which the bearing extraction member is in the form of a plug 116 mounted in a blind hole 118 in a shell 112 which is otherwise the same as shell 12 of FIG. 1. After the drilling step described above with reference to FIG. 2, bearing 114 can be extracted with the aid of a simple T-handle with a shaft threaded as its distal end to match the threads of plug 116. The end of the T-handle shaft is screwed into plug 116 until it bottoms out in the blind hole, after which further turning of the handle draws the plug out of the hole and thereby causes the bearing to disengage from the shell. A number of spikes 119 may be provided to engage the polyethylene and thereby resist spinning of the plug as the handle is turned. The hole is thereafter plugged with a replacement plug such as that shown in FIG. 6 but correspondingly shorter in axial length.

Figure 8:
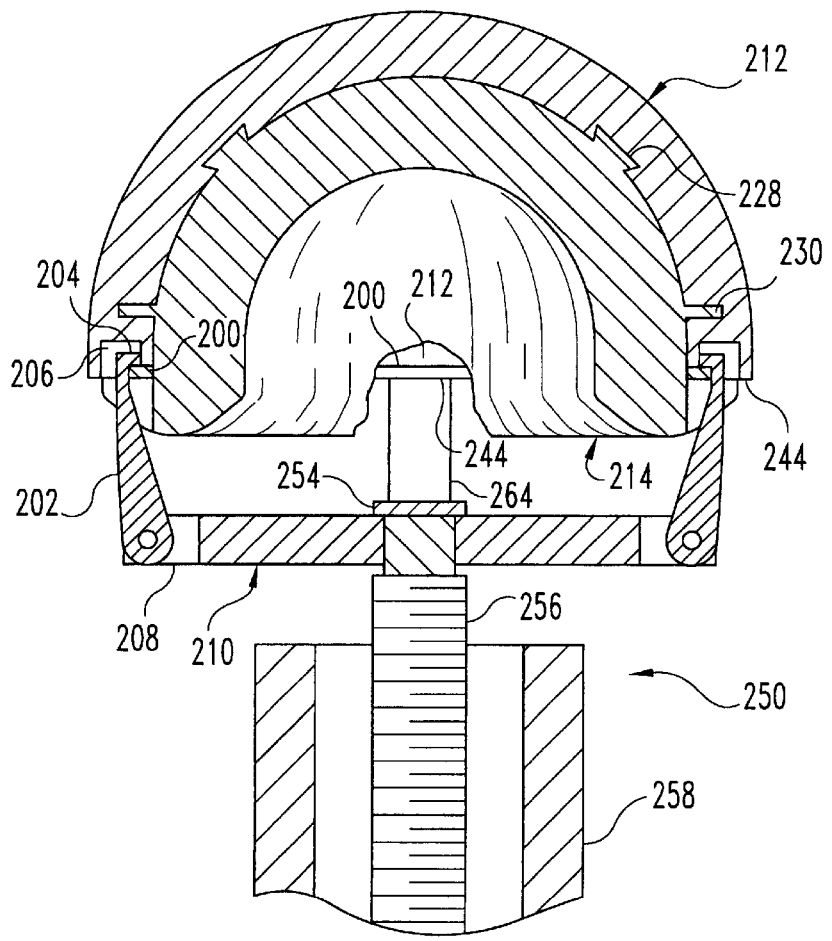
FIG. 8 is a cross-sectional side view of another embodiment of an acetabular cup assembly according to the present invention in conjunction with another bearing extractor.

Referring to FIG. 8, another contemplated bearing extraction member is a peripheral ring 200 located in an annular recess provided for this purpose in the face 244 of shell 212. Bearing 214 in this embodiment may be extracted with the aid of an extractor 250 that is a modified form of the extractor of FIG. 3. In this case, the extractor includes a pair of puller arms 202 with inwardly turned fingers 204 which are inserted into respective blind holes 206 in face 244 and moved inwardly to engage the back side of ring 200 as illustrated in FIG. 8. The puller arms may be pivotally mounted on opposite forked ends 208 of a bar 210 that is rotatably mounted and axially constrained on the distal end 254 of a drive screw 256 that, except as shown at its distal end, is the same as drive screw 56 of FIG. 3. Extractor 250 is otherwise the same as extractor 50 of FIG. 3, although it is shown rotated 90° with respect to the view of FIG. 3, and includes a pair of arms 264, only one of which appears in FIG. 8, on the distal end of casing 258 to brace the extractor against the face 244 of shell 212. Bearing 214 is partially cut away in FIG. 8 to illustrate the contact. Arms 264 contact the face of the shell at the outer periphery thereof, as with arms 64 in FIG. 3, and thus do not contact ring 200 which is at the inner periphery of the shell. In operation, arms 264 are preferably oriented 90° apart from puller arms 202 as shown in the drawing. It will be appreciated from the foregoing that three or more puller arms 202 and corresponding holes 206 may be provided for engagement with ring 200, with the holes preferably equally spaced about the circumference of face 244. A like number of arms 264 is preferably provided for bracing, also equally spaced and positioned halfway between adjacent puller arms. Dovetails 228 and an annular groove 230 of the type described above with reference to FIG. 1 may be provided in the shell, although groove 230 is positioned farther from the face of the shell in this embodiment because of the two blind holes 206. Bearing 214 is preferably direct compression molded into shell 212 and onto the face of the shell over ring 200 except at holes 206, which are covered during the molding process to keep them clear of polyethylene and to maintain access thereto.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, an implanted bearing extraction member in the form of an unthreaded plug or plate may be provided with a keyhole for receiving a correspondingly shaped key on the nose portion of the extractor, the key and keyhole cooperating to form a twist lock mechanism whereby the extractor may engage a distal surface of the unthreaded bearing extraction member and pull it outwardly. Also, plug locations other than in an apical hole or any hole in the shell are contemplated, as are multiple plugs, plates and the like. In addition, other forms of retainers, other methods of securing a bearing, and other methods of removing a bearing without removing the base member are contemplated, as described in U.S. Pat. No. 6,280,476, which is hereby incorporated by reference in its entirety.

What is claimed:

1. A hip joint prosthesis with an integral bearing extraction member, comprising:

an acetabular cup having a modular bearing retainer;

a primary bearing direct compression molded to said acetabular cup; and implantable means for removing said molded primary bearing from said acetabular cup substantially in one piece without disturbing said acetabular cup.

2. The prosthesis of claim 1, wherein said removing means includes a plug mounted in said acetabular cup, and wherein said primary bearing is directly molded over said plug.

3. The prosthesis of claim 2, wherein said plug is internally threaded.

4. The prosthesis of claim 3, wherein said primary bearing is molded into said internally threaded plug.

5. A hip joint prosthesis with an integral bearing extraction member, comprising:

an acetabular cup;

a bearing extraction member mounted in said acetabular cup, said bearing extraction member including an opening therein for engaging an extraction tool to be inserted during a revision procedure; and a primary bearing direct compression molded into said acetabular cup and into said opening in said bearing extraction member.

6. The prosthesis of claim 5, wherein said bearing extraction member is recessed in said acetabular cup.

7. The prosthesis of claim 6, wherein said bearing extraction member includes a plug positioned in a hole in said acetabular cup, and wherein said primary bearing is directly molded over said plug.

8. The prosthesis of claim 5, wherein said bearing extraction member is internally threaded.

9. The prosthesis of claim 7, wherein said acetabular cup has a surface defining a retainer for a modular bearing.

10. A hip joint prosthesis with an integral bearing extraction member, comprising:

an acetabular cup having a modular bearing retainer adapted to cooperate with an auxiliary mechanical locking element to securely retain a modular bearing in said acetabular cup;

a primary bearing direct compression molded to said acetabular cup; and implantable means for removing said primary bearing from said acetabular cup substantially in one piece without disturbing said acetabular cup.

11. A hip joint prosthesis with an integral bearing extraction member, comprising:

an acetabular cup;

a primary bearing secured to said acetabular cup; and a bearing extraction member mounted in said acetabular cup in contact with said primary bearing, wherein said bearing extraction member is recessed in said acetabular cup, wherein said bearing extraction member includes a ring, and wherein said primary bearing is directly molded over said ring.

12. A method of replacing a hip joint, comprising:

providing an acetabular cup with a retainer for a modular replacement bearing to be secured to said acetabular cup after removal of a primary bearing therefrom;

providing a bearing extraction member in said acetabular cup;

direct compression molding a primary bearing to said acetabular cup; and implanting said acetabular cup, with said retainer, primary bearing and bearing extraction member, in a patient during primary hip replacement surgery.

13. A method of replacing a hip joint, comprising:

providing an acetabular cup with a retainer for a modular replacement bearing to be secured to said acetabular cup after removal of a primary bearing therefrom;

providing a bearing extraction member in said acetabular cup;

securing a primary bearing to said acetabular cup;

implanting said acetabular cup, with said retainer, primary bearing and bearing extraction member, in a patient during primary hip replacement surgery;

removing said primary bearing during revision surgery without removing said acetabular cup; and securing a modular bearing to said retainer during said revision surgery.

14. A method of replacing a hip joint, comprising:

providing a bearing extraction member in an acetabular cup;

direct compression molding a primary bearing to said acetabular cup; and implanting said acetabular cup, with said bearing extraction member and said primary bearing therein, in a patient during primary hip replacement surgery.

15. A method of replacing a hip joint, comprising:

providing a bearing extraction member in an acetabular cup;

securing a primary bearing to said acetabular cup;

implanting said acetabular cup, with said bearing extraction member and said primary bearing therein, in a patient during primary hip replacement surgery;

attaching an extraction tool to said bearing extraction member;

actuating said bearing extraction member with said extraction tool to extract said primary bearing from said acetabular cup; and securing a secondary bearing to said acetabular cup after removal of said primary bearing therefrom.

16. A hip joint replacement system, comprising:

an acetabular cup;

a primary bearing secured to said acetabular cup;

a bearing extraction member mounted in said acetabular cup in contact with said primary bearing; and extraction instrumentation including means for engaging said bearing extraction member and means for engaging said acetabular cup at a point spaced from said bearing extraction member.

17. The hip joint replacement system of claim 16, wherein said means for engaging said bearing extraction member and said means for engaging said acetabular cup are mechanically interconnected.

* * * * *